US010053682B2

(12) United States Patent
Zhang et al.

(10) Patent No.: US 10,053,682 B2
(45) Date of Patent: Aug. 21, 2018

(54) β-GALACTOSIDASE MUTANT WITH HIGH TRANSGLYCOSIDASE ACTIVITY, AND PREPARATION METHOD THEREOF AND USES THEREOF

(71) Applicant: BIOTECHNOLOGY RESEARCH INSTITUTE, CHINESE ACADEMY OF AGRICULTURAL SCIENCES, Beijing (CN)

(72) Inventors: Wei Zhang, Beijing (CN); Yuhong Zhang, Beijing (CN); Bo Liu, Beijing (CN); Ning Sun, Beijing (CN); Jialin Zhang, Beijing (CN)

(73) Assignee: BIOTECHNOLOGY RESEARCH INSTITUTE, CHINESE ACADEMY OF AGRICULTURAL SCIENCES, Beijing (CN)

( * ) Notice: Subject to any disclaimer, the term of this patent is extended or adjusted under 35 U.S.C. 154(b) by 0 days.

(21) Appl. No.: 15/304,078

(22) PCT Filed: Apr. 7, 2015

(86) PCT No.: PCT/CN2015/075942
§ 371 (c)(1),
(2) Date: Oct. 14, 2016

(87) PCT Pub. No.: WO2015/158213
PCT Pub. Date: Oct. 22, 2015

(65) Prior Publication Data
US 2017/0204389 A1 Jul. 20, 2017

(30) Foreign Application Priority Data
Apr. 14, 2014 (CN) .......................... 2014 1 0148999

(51) Int. Cl.
C12N 9/38 (2006.01)
C12N 9/24 (2006.01)
C12N 9/14 (2006.01)
C12P 21/06 (2006.01)
C12P 19/34 (2006.01)
C12N 1/00 (2006.01)
C12N 15/00 (2006.01)
C07H 21/04 (2006.01)
C07K 1/00 (2006.01)

(52) U.S. Cl.
CPC .... C12N 9/2471 (2013.01); C12Y 302/01023 (2013.01)

(58) Field of Classification Search
CPC .................. C12N 9/2471; C12Y 302/01023
USPC ...... 435/207, 195, 69.1, 91.1, 320.1, 254.11, 435/200; 536/23.1, 23.2; 530/350
See application file for complete search history.

(56) References Cited

U.S. PATENT DOCUMENTS 5,736,374 A * 4/1998 Berka ............ C12Y 302/01023
435/207

FOREIGN PATENT DOCUMENTS

CN 101948854 A 1/2011
CN 102337254 A 2/2012
KR 20070101488 A 10/2007
WO WO2014/081884 A1 * 5/2014

OTHER PUBLICATIONS

Broun et al., Catalytic plasticity of fatty acid modification enzymes underlying chemical diversity of plant lipids. Science, 1998, vol. 282: 1315-1317 (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Haibo Xu, "Characterization and Site-Directed Mutagenesis of α-Galactosidase", Basic Sciences, China Master's Theses Full-Text Database, No. 2, Feb. 15, 2014, pp. 1-81, see the whole document.
Hung M.N. et al., "Purification and Characterization of a Recombinant β-Galactosidase with Transgalactosylation Activity from Bifidobacterium Infantis HL 96", Appl Microbiol, Biotechnol. , 2002, vol. 58: 439-445.
Mozaffar Zahid et al., "Continuous production of galacto-oligosaccharides from lactose using immobilized β-galactosidase from Bacillus circulans", Appl Microbiol Biotechnol, 1986, vol. 25:224-228.

(Continued)

Primary Examiner — Ganapathirama Raghu
(74) Attorney, Agent, or Firm — Gokalp Bayramoglu

(57) ABSTRACT

The present invention relates to the field of genetic engineering and hereditary engineering. The present invention discloses a β-galactosidase (β-galactoside galactohydrolase, EC 3.2.1.23) mutant with high transglycosidase activity, which is obtained by single-site-saturation mutation of amino acid sequences of β-galactosidase from Aspergillus candidus and Aspergillus oryzae, with own signal peptides removed. The transglycosidase activity of the mutant is over 15% higher than that of wild types. Meanwhile, the present invention also discloses a DNA molecule which encodes the mutant, a recombinant expression vector containing the DNA molecule, and a host cell expressing the DNA molecule. In addition, the present invention also provides a method for preparing β-galactosidase mutant with high transglycosidase activity by using the recombinant expression vector and applications of the mutant, the DNA molecule, the recombinant expression vector and the host cell in preparation of β-galactosidase.

12 Claims, 4 Drawing Sheets

(56) References Cited

OTHER PUBLICATIONS

Jorgensen F. and Hansen O.C. et al., "High-efficiency synthesis of oligosaccharides with a truncated β- galactosidase from Bifidobacterium bifidum", Appl Microbiol Biotechnol, 2001, vol. 57: 647-652.

Placier G. et al., "Evolved β-Galactosidases from Geobacillus stearothermophilus with Improved Transgalactosylation Yield for Galacto-Oligosaccharide Production", Applied and App. Environ. Microbiol., 2009, vol. 7 (19): 6312-6321.

Yufei Wu et al., "Enhancing the production of galacto-oligosaccharides by mutagenesis of Sulfolobus solfataricus β-galactosidase", Food Chemistry 138, 2013, pp. 1588-1595, see the whole document.

Maksimainen Mirko M. et al., "The crystal structure of acidic β-galactosidase from Aspergillus oryzae", International Journal of Biological Macromolecules 60, 2013, pp. 109-115 see the whole document.

\* cited by examiner

β-GALACTOSIDASE MUTANT WITH HIGH TRANSGLYCOSIDASE ACTIVITY, AND PREPARATION METHOD THEREOF AND USES THEREOF

CROSS REFERENCE TO RELATED APPLICATIONS

This application is a national phase entry and claims the priority of International Application No. PCT/CN2015/075942, filed on Apr. 7, 2015, which is based upon and claims priority to NO. CN2014108999.4, filed on Apr. 14, 2014, the entire contents of which are incorporated herein by reference.

TECHNICAL FIELD

The present invention relates to the field of genetic engineering and hereditary engineering. The present invention discloses a β-galactosidase (β-D-galactoside galactohydrolase, EC 3.2.1.23) mutant with high transglycosidase activity, a preparation method thereof, and uses thereof.

BACKGROUND OF THE INVENTION

Galactooligosaccharides (GOS) are a kind of oligosaccharides which cannot be digested and absorbed by the gastrointestinal tracts of human bodies, but directly enter the large intestine to be well utilized by various *Bifidobacterium*, and have special biological functions. GOS can improve the micro-ecological environment in the human body, aid multiplication of *Bifidobacterium* and other beneficial bacteria, and improve immunity of the human body. Meanwhile, GOS generate organic acids through metabolism to decline the pH value in tracts, to restrain the growth of *salmonella* and putrefying bacteria in the tracts, to reduce toxic fermented products and hazardous bacterial enzymes, to adjust gastrointestinal functions, thus reducing burdens on livers for decomposition of toxins. GOS have properties better than those of other functional oligosaccharides and therefore are more conveniently and easily applied to various fields as additives. GOS can be adapted to more food varieties and wider consumer groups, and have a huge application value and a huge market prospect.

GOS are usually prepared by five methods, namely extraction from natural materials, acid hydrolysis of natural polysaccharides, chemical synthesis, fermentation and enzymatic synthesis. GOS merely exist in nature, are color-less, have no charge, and therefore are difficultly extracted and separated. Products converted from the natural polysaccharides have a low yield, are complicated in elements and hard to be purified. The chemical synthesis tends to generate a lot of toxins and residues, causing serious environmental pollution. The fermentation method for producing the GOS is rarely studied, is still in the laboratory stage, and fails to realize mass production. At present, the industrial production of the GOS is completed through β-galactosidase (β-D-galactoside galactohydrolase, EC 3.2.1.23). β-galactosidase, also called lactase, has dual activities, namely hydrolysis and transglycosylation. Previously, studies on the β-galactosidase mainly focus on utilization of the hydrolysis function thereof to produce low lactose milk products to relieve various side effects such as diarrhea and abdominal distension of lactose-intolerant patients caused by taking milk products. Since the special health-care functions of the GOS have been determined, production of the GOS by the transglycosidase effect of the β-galactosidase has become a study hotspot. The study mainly focuses on the three following aspects:

1. Screening of Strains for Generating the β-Galactosidase with High Transglycosidase Activity Various microorganisms including yeasts, *Bacillus*, *Aspergillus*, *Penicillium* and Bifidobacteria, all have β-galactosidase with transglycosidase activity. Studies show that, due to different enzymatic properties, β-galactosidase coming from different sources vary with reactions conditions for synthesizing the GOS. β-Galactosidase can be classified into acidic type and neutral type according to the optimum pH values. Usually, β-galactosidase sourced from mold is acidic enzyme, with the best performance at a pH value in a range of 2.5-5.5 and at a relatively high temperature (50-60° C.); β-Galactosidase generated by yeasts and bacteria is neutral enzyme, with the best performance at a pH value in a range of 6-7.5 and at a relatively low temperature (30-40° C.). β-Galactosidase generated by different sources work on different substrates, and the types and ratios of oligosaccharide in the generated GOS are also diversified, so the new GOS verities emerge in endlessly. Even so, the screened β-galactosidase generally has low transglycosidase activity. Moreover, the highest yield of the GOS is usually 5-30%, failing to meet the demands of industrial production.

2. Optimization of Reaction Conditions and Improvement of Production Process

Some researchers tried to overcome the defect of low transglycosidase activity through optimizing the production conditions and processes of the GOS to enhance the yield of the GOS, and have made some achievements. Main methods include: increase in concentration of the initial lactose, control over the water activity using organic solvents and use of the immobilization technology. The hydrolysis and transglycosylation reaction of the β-galactosidase are inversible. When the substrate (lactose) concentration is low, the concentration of the hydrolysis product, namely galactose, is low, and the galactose has a limit effect on restraining the hydrolysis enzymatic activity. In such circumstances, the β-galactosidase represents high hydrolysis activity, while the transglycosylation activity is low, so the content of monosaccharides contained in the product is relatively high. When the lactose concentration is relatively high, the concentration of the hydrolysis product, namely the galactose, is relatively high, and the galactose reaching a certain value can restrain the hydrolysis enzymatic activity. The galactose is the substrate of the transglycosidase, and the high galactose concentration aids synthesis of galactooligosaccharide, and the product has a high content of oligosaccharide. Using organic solvents is good for composition of the oligosaccharide because organic solvents can reduce the water activity in the reaction system to affect the activity site and reaction mechanism of the enzyme, to induce the hydrolase to catalyze inverse transglycosylation, and to deviate the reaction balance from hydrolysis to oligosaccharide synthesis. Using the immobilization technology can greatly increase the pH and thermal stability of free enzymes, and can realize recycling and reduce production cost. Mozaffar was reported that β-galactosidase is absorbed to phenolic resin and then is cross-linked with glutaraldehyde, and then the yield of the oligosaccharide is enhanced by 20%. However, some studies find that when an immobilized enzyme is applied to the lactose solution with a relatively high concentration, the yield of the oligosaccharide is smaller than that the yield of the oligosaccharide generated when the free enzyme is used. Thus it can be seen that problems cannot always be radically solved simply by optimizing conditions.

3. Genetic Engineering to Enhance Expression of the β-Galactosidase and to Improve its Properties In the natural world, the yield of GOS by wild β-galactosidase is generally maintained in the range of 20-45%. The low yield fails to meet production demands, screening excellent transglycosidase mutant enzyme through molecular modification has become a research hotspot. Hansen O. (2001) found that after Bifidobacteria β-galactosidase BIF3 is deleted with 580 amino acids at a C-terminal, the protein is converted into an efficient transglycosidase which can generate GOS by using almost 90% of lactose, while hydrolysis elements account for 10%. When the lactose concentration is in the range of 10%-40%, the ratio of the transglycosidase activity to the hydrolysis activity is always maintained at 9:1. In 2009, Placier G. carried out directed revolution on the β-galactosidase sourced from *Geobacillus stearothermophilus* KVE39, and successfully obtained three strains of mutants R109W, R109V and R109K on the screen strategy of enhancing the transglycosidase activity while reducing the hydrolysis activity. In 18% (w/v) lactose, the yield of oligosaccharide generated by three mutants was 23%, 11.5% and 21%, respectively. In wild enzyme, the oligosaccharide yield was 2% only. Wu Y. (2013) modified molecules of the β-galactosidase sourced from *Sulfolobus acidocaldarius* to study the most appropriate generation conditions of GOS. Under respective most appropriate conditions, the GOS yield of the mutant F441Y was 61.7%, F359Q was 58.3%, and the wild enzyme was 50.9%.

However, so far, the screening and separation as well as process optimization of the natural enzymes, and genetic engineering to enhance the expression of the β-galactosidase and improve properties both fail to change the current states of low transglycosidase activity and low yield of the β-galactosidase, resulting in low synthesis yield of the GOS and extremely high production cost which seriously restrain the low-cost production, promotion and application of the GOS.

Therefore, creating a novel β-galactosidase with high transglycosidase activity and low-cost production are two of main problems to be solved urgently in the current research and production.

SUMMARY OF THE INVENTION

Aiming at the defects mentioned above, on the one hand, the present invention provides a β-galactosidase mutant with high transglycosidase activity, which is obtained by single-site-saturation mutation of β-galactosidase from *Aspergillus candidus* or *Aspergillus oryzae*, preferably obtained through single-site-saturation mutation of an amino acid sequence as shown in SEQ ID NO: 2 or SEQ ID NO: 4, wherein transglycosidase activity of the mutant is over 15% higher than that of the wild types, preferably over 20%, and more preferably over 30%.

In an optimal implementation scheme of the present invention, the sites where mutation occurs include an amino acid at site 219, an amino acid at site 245 or an amino acid at site 785.

In a further optimal implementation scheme of the present invention, the single-site-saturation mutation is respectively involved in replacement of serine residues (S219G) at site 219 by glycine residues, replacement of serine residues (S219E) at site 219 by glutamic acid residues, replacement of serine residues (S219F) at site 219 by phenylalanine residues, replacement of serine residues (S219V) at site 219 by valine residues, replacement of serine residues (S219A) at site 219 by alanine residues, replacement of phenylalanine residues (F245R) at site 245 by Arginine residues, replacement of phenylalanine residues (F245K) at site 245 by lysine residues, replacement of phenylalanine residues (F245G) at site 245 by lysine residues, replacement of phenylalanine residues (F245S) at site 245 by serine residues, or replacement of glutamic acid residues (E785V) at site 785 by valine residues.

On another hand, the present invention provides a DNA molecule encoding the mutant.

On another hand, the present invention provides a recombinant expression vector containing the DNA molecule, preferably a recombinant yeast expression vector.

On another hand, the present invention provides a host cell expressing the DNA molecule, preferably strains of *saccharomyces, kluyveromyces, schizosaccharomyces* and methylotrophic yeasts, wherein the methylotrophic yeast strains are preferably *Pichia pastoris* strains.

On another hand, the present invention provides a method for preparing β-galactosidase mutant with high transglycosidase activity, including the following steps:

1. transformation the host cell by using the recombinant expression vector according to the claims above to obtain recombinant strains;

2. culturing the recombinant strains to induce expression of the recombinant β-galactosidase protein;

3. gathering and purifying the expressed β-galactosidase mutant with high transglycosidase activity.

At last, the present invention provides applications of the mutant, the DNA molecule, the recombinant expression vector and the host cell in preparation of β-galactosidase.

The present invention adopts the single-site-saturation mutation technology to perform site-saturation mutation on the β-galactosidase gene lacb', with its own signal peptides removed, of the *Aspergillus candidus* and the β-galactosidase gene laco', with own signal peptides removed, of the *Aspergillus oryzae*, and obtains the β-galactosidase mutant with high transglycosidase activity, so the transglycosidase activity of the mutant is over 15% higher than that of wild types, and even over 30% higher. Therefore, the preparation of the β-galactosidase mutant with high transglycosidase activity becomes true, which lays a good foundation for applications of the β-galactosidase in GOS production.

DETAILED DESCRIPTION OF THE EMBODIMENTS

Figure 1:
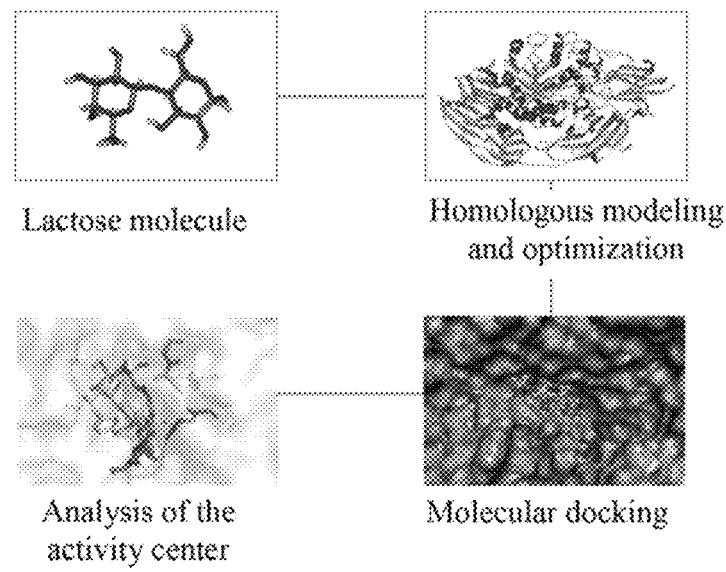
FIG. 1: Process of molecular docking between the β-galactosidase of *Aspergillus candidus, Aspergillus oryzae* with substrates.

The present invention is described in further detail in conjunction with embodiments which are used for describing the present invention, not limiting the present invention. It should be pointed out that, for those skilled in this field, various improvements and modifications can be made on the present invention according to the principle of the present invention. Those improvements and modifications shall also fall within the protective scope of the present invention.

Embodiment 1: Tertiary Structure of the β-Galactosidase and the Prediction of Mutation Sites β-Galactosidase gene lacb' with own signal peptide removed was obtained by the laboratory through cloning from *Aspergillus candidus*. The gene with own signal peptide sequence removed consists of 2,958 nucleotides, with a specific sequence as shown in SEQ ID NO: 1. A protein encoded by the gene consists of 986 amino acids, with a specific sequence as shown in SEQ ID NO: 2.

β-Galactosidase gene laco' with own signal peptide removed was obtained by the laboratory through cloning from *Aspergillus oryzae*. The gene also consists of 2,958 nucleotides, with a specific sequence is as shown in SEQ ID NO: 3. A protein encoded by the gene also consists of 986 amino acids, with a specific sequence as shown in SEQ ID NO: 4. The sequence of the amino acids was different from the protein encoded by the gene lacb' in only three amino acids at site 231: lacb' (Gly), laco' (Ser); site 401: lacb' (Met), laco' (Ile); and site 970: lacb' (Asp), laco' (Asn).

The β-galactosidase of the *Aspergillus candidus* and the *Aspergillus oryzae* was used as the research material. Crystal structure of β-galactosidase (PDB login No.: 1TG7) from *Penicillium*, crystal structure of β-galactosidase (PDB login No.: 4IUG) from *Aspergillus oryzae* and a protein crystal structure of β-galactosidase (PDB login No.: 3OG2) from *Trichoderma reesei* were used as homologous models to predict the 3D structure of the β-galactosidase and its docking areas with substrates. The predicted structures were highly similar to the prediction results reported in literatures (See The crystal structure of acidic β-galactosidase from *Aspergillus oryzae*, Mirko M. Maksimainen, International Journal of Biological Macromolecules, 2013, 109-115). The protein consisted of five structural domains: structural domain 1 (amino acids 1-394) close to terminal N was the activity center of the enzyme, wherein the activity center was a TIM barrel-type structure. Structural domain 2 (amino acids 395-573) consisted of 16 reverse parallel β-pleated sheets and 1 α-helix, containing a structural sub-domain similar to the immune globulin; structural domain 3 (amino acids 574-661) consisted of a β-interlayer, which was comprised of 8 reverse parallel β-pleated sheets and was shaped like a "Greek key", and 1 α-helix; structural domain 4 (amino acids 662-857) and structural domain 5 (amino acids 858-1005) were consisted of "spring roll" shaped topological structures. Through focused analysis of the activity center, it was found that, Glu160 and Glu258, respectively on the fourth and the seventh β-pleated sheets of the TIM barrel-type activity center might be acid acids which were necessary for catalytic reaction, while Asn140 and Tyr96 might be used for immobilizing lactose molecules.

Figure 2:
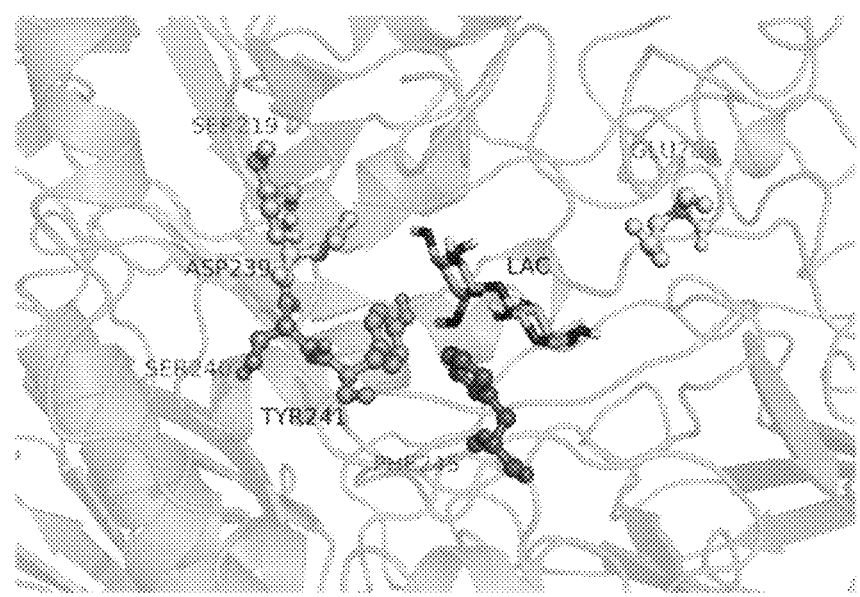
FIG. 2: Position relationship among the mutation sites of the β-galactosidase of the *Aspergillus candidus* and the *Aspergillus oryzae* with lactose in molecular space.

According to the 3D structure of the obtained β-galactosidase, software Discovery Studio was used to simulate the molecular docking of the enzyme and the substrate (see FIG. 1), and by analyzing the docking results, the amino acids interacting with the substrate might be known (see FIG. 2). Computational biological software was used to evaluate the evolution entropies of the amino acids one by one, and six amino acid sites, S219, D239, S240, Y241, F245 and E785 (see table 1), with large changes in the evolution entropy were finally screened and determined to carry out site-saturation mutation.

TABLE 1

Entropies of typical amino acids of the β-galactosidase

| Amino acid | Amino acid site | Evolution entropy |
| --- | --- | --- |
| S | 219 | 0.8114 |
| D | 239 | 0.6678 |
| S | 240 | 0.8581 |
| Y | 241 | 0.8374 |
| F | 245 | 0.8594 |
| E | 785 | 0.288 |

Embodiment 2: Construction of Single-Site-Saturation Mutant Library of *Pichia pastoris*

1. Materials and Method (1) Strains and Plasmid

Wild genes were sourced from β-galactosidase gene lacb', with own signal peptide removed, of *Aspergillus candidus*, and the β-galactosidase gene laco' of the *Aspergillus oryzae*, which were obtained by previous cloning in the laboratory. The specific sequences can be seen in SEQ ID NO: 1 and SEQ ID NO: 3, respectively. The wild genes were connected to pPIC9 expression vectors, and were expressed in the *Pichia pastoris* GS115. *Escherichia coli* Trans1-T1 competent cells were brought from TransGen Corporation Ltd. pPIC9 expression vectors and *Pichia pastoris* GS115 were brought from Invitrogen Corporation Ltd.

(2) Culture Mediums and Preparation of Related Solutions

For transformation, culture and screening of the *Pichia pastoris*, conventional culture mediums and reagents, refer to the *Pichia* Expression Kit manual of Invitrogen Corporation Ltd.

PTM trace salts: 0.6% $CuSO_4$, 0.008% $NaI_2$, 0.3% $MnSO_4$, 0.02% $Na_2MoO_4$, 0.002% $H_3BO_3$, 0.05% $CoCl_2$, 2% $ZnCl_2$, 6.5% $FeSO_4$ and 0.5% sulfuric acid (v/v).

Fermentation base salt medium (FBSM): 0.5% $KH_2PO_4$, 5% $NH_4H_2PO_4$, 1.485% $MgSO_4$, 1.82% $K_2SO_4$, 0.093% $CaSO_4$, 0.15% KOH, 0.00011% Biotin, 0.44% PTM trace salts, and 2% glucose.

Fermentation base induction medium (FBIM): 0.5% $KH_2PO_4$, 5% $NH_4H_2PO_4$, 1.485% $MgSO_4$, 1.82% $K_2SO_4$, 0.093% $CaSO_4$, 0.15% KOH, 0.00011% Biotin, 0.44% PTM trace salts and 0.5% methanol.

$Na_2HPO_4$-citric acid buffer solution (0.1 mol/L, pH5.2): 536 mL of 0.2 mol/L $Na_2HPO_4$, 464 mL of 0.1 mol/L citric acid were mixed uniformly, with a pH value adjusted to 5.2.

(3) Oligonucleotides Primer

Specific primers used in the gene mutation can be seen in table 2.

TABLE 2

List of primers used in gene mutation

| Primer position | Primer name | Primer sequence (5'-3', mutated basic group underlined) |
|---|---|---|
| 5' terminal and 3' terminal of gene | Bgl-down(A) (SEQ ID NO: 5) | CGCGAGGCAGAGATCTTGAGATAAATTTCACG |
| | Bgl-down-Com(D) (SEQ ID NO: 6) | ACGTGAAATTTATCTCAAGATCTCTGCCTCGCG |
| Library S219 | 219-up($B_{219}$) (SEQ ID NO: 7) | ACTTCCAGGAGCATTGTGCCCAGAAGGMNNGGCATCGTTG |
| | 219-down($C_{219}$) (SEQ ID NO: 8) | TTCTGGGCACAATGCTCCTGGAAGTGGAACG |
| Library D239 | 239-up($B_{239}$) (SEQ ID NO: 9) | TGCGCAATCAAAGCCAAGGGGATAGCTMNNGTGACC |
| | 239-down($C_{239}$) (SEQ ID NO: 10) | TCCCCTTGGCTTTGATTGCGCAAACCC |
| Library S240 | 240-up($B_{240}$) (SEQ ID NO: 11) | TGCGCAATCAAAGCCAAGGGGATAMNNATCGTGACC |
| Library Y241 | 241-up($B_{241}$) (SEQ ID NO: 12) | TTTGCGCAATCAAAGCCAAGGGGMNNGCTATC |
| | 241-down($C_{241}$) (SEQ ID NO: 13) | TGGCTTTGATTGCGCAAACCCATCCGTATG |
| Library F245 | 245-up($B_{245}$) (SEQ ID NO: 14) | ATACGGATGGGTTTGCGCAATCMNNGCCAAG |
| | 245-down($C_{245}$) (SEQ ID NO: 15) | TGCGCAAACCCATCCGTATGGCCC |
| Library E785 | 785-up($B_{785}$) (SEQ ID NO: 16) | TTTCCTCGCCGACCGTCCAATTAACGTCG |
| | 785-down($C_{785}$) (SEQ ID NO: 17) | TGGACGGTCGGCGAGGAAACCATGAAG |

2. Amplification of Mutation Sites Using Overlap PCR

Figure 3:
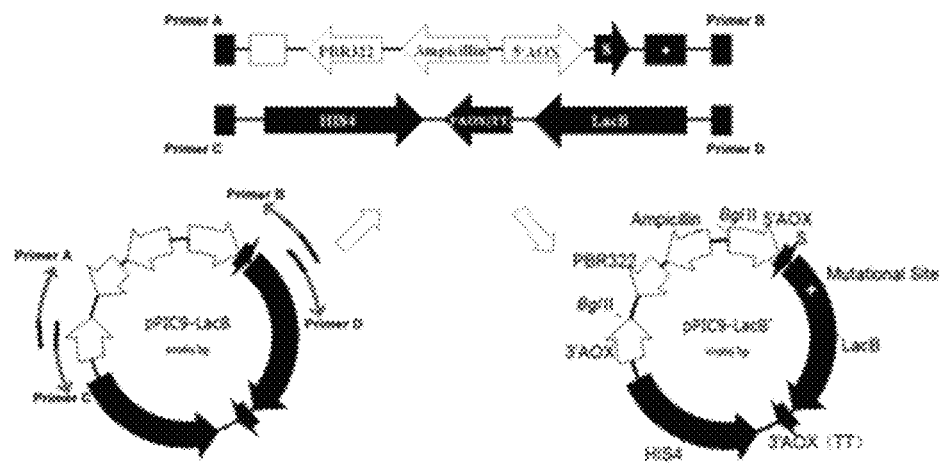
FIG. 3: Construction process of a recombinant expression vector containing the gene of the mutant, namely the β-galactosidase.

Overlap PCR was adopted to perform saturation mutation on single site. This means that two segments were respectively amplified by PCR, and then extended in an overlapped way to be fused. A pair of compatible primers was designed where was overlapped in a certain extent nearby a target point (refer to primers B, C in FIG. 3). The primers were respectively combined with primers at terminals 5' and 3' of the gene (refer to primers A, D in FIG. 3). Upstream segments and downstream segments containing the target point were amplified. Those primers were complementary, so the produced PCR product chains were mutually overlapped. The Upstream segments and downstream segments were crossed at the target point, and extended in an overlapped way with template to each other to obtain full-length genes. 1 μL of pPIC9-lacb' plasmids were taken as template, primer pairs A and C, B and D were respectively amplified by using TransStart FastPfu DNA polymerase. PCR products were tested with agarose gel electrophoresis. Segments with correct sizes were recycled (for the method, refer to the agarose gel DNA extraction kit of TIANGEN Corporation Ltd).

3. In-Vivo Homologous Recombination for Construction of the Expression Vector

Two PCR segments with homologous arms are mixed with an equal molar weight, and then added with homologous recombinase to perform in-vivo recombination. The mixture reacted for 30 min at the temperature of 25° C. and then placed on ice for 5 min. Then the transformation shall occur immediately or the product shall be stored at a temperature of –20° C. 10 μL of the homologous recombination product was taken and chemically transferred into 100 μL of Trans1-T1 competent cells of the Escherichia coli; the mixed substance was coated on a LB plate containing ampicillin. Then the plate was culture overnight at a temperature of 37° C.

Mutation in an amount of 3-5 times the theoretical quantity (mutation codon was MNN; the theoretical value of the mutant library was 4×4×2=32; 32 single-site-saturation mutated clones could cover all mutants) growing from the LB plate could coverage mutation sites. 6-8 individual clones were randomly selected from the LB plate of each mutation library to measure the DNA sequence. The measurement was entrusted to MedicalBio Corporation Ltd. The mutant librarys were respectively named as library S219, library D239, library S240, library Y241, library F245 and library E785 according to mutation sites.

4. Expression of the β-Galactosidase Mutant and Screening Method of Strains with High Transglycosidase Activity (1) Expression of the Recombinant Plasmids in the Pichia pastoris Mixed plasmids (about 200-230 μg) in the Escherichia coli were extracted from each mutant library, completely digested by using sufficient Bgl II restriction enzymes, then settled with propanol, washed by 70% ethanol, and then dissolved in de-ionized water to transform the Pichia pastoris. The transformed Pichia pastoris was coated on an MM plate containing x-gal. Blue strains on the MM plate were positive clones of the β-galactosidase, and corresponding strains on an MD plate were transferred into a 48-hole culture plate. Different mutants were cultured with the FBSM first, then grew quickly for 48 h in the 48-hole plate and next cultured in an inducing manner with the FBIM. The supernatant of the cultured product was taken to measure the β-galactosidase activities of the positive strains.

(2) Method for Measuring Activity of the β-Galactosidase Adopting oNPG Substrate 0.1 g of o-nitrophenyl-β-D-galactopyranoside (oNPG) substrate was accurately weighed and dissolved in 40 mL of Na$_2$HPO$_4$-citric acid buffer solution (pH 5.2, 0.1 mol/L). Then, oNPG solution with a concentration of 0.25% (W/V) was obtained. The crude enzyme solution to be measured was diluted with the 0.1 mol/L Na$_2$HPO$_4$-citric acid buffer solution to a proper factor. 800 μL of substrate solution was added into a test tube and then was preheated for 2 min in a water bath at a temperature of 60° C. 200 μL of diluted enzyme solution was added and then mixed uniformly. 1 mL of 10% trichloroacetic acid (TCA) was added to end the reaction after the reaction proceeded for 15 min first; then 2 mL of 1 mol/L Na$_2$CO$_3$ was added for coloration; and next the optical density (OD$_{420\ nm}$) was measured at 420 nm. The Na$_2$HPO$_4$-citric acid buffer solution (pH 5.2, 0.1 mol/L) was used as a blank reference, and a standard curve was employed to calculate the amount of the generated oNP. Then, the activity of the β-galactosidase could be calculated. Definition of enzymatic activity unit: one unit of the β-galactosidase activity is defined as the enzyme amount required that can catalyze oNPG to generate 1 μmol o-nitrophenol (oNP) every minute at the temperature of 60° C. and at the pH of 5.2.

According to the result obtained from the standard curve of the β-galactosidase, the calculation formula of the enzymatic activity is:

$$\text{Enzymatic activity (U/mL)} = 5*N*(0.9472X+0.0046)/15$$

X: optical density (OD$_{420\ nm}$) of the reaction; N: dilution factor of the enzyme solution; 15: 15 min reaction time; 5: converting the enzymatic activity in 200 μL of diluted enzyme solution into 1 mL.

(3) Basic Reaction System and Reaction Conditions for Measurement of the Transglycosidase Activity of the Mutated-Protein The crude enzyme solution of each mutant was diluted by 0.1 mol/L Na$_2$HPO$_4$-citric acid buffer solution with a pH value of 5.2 to reach an equivalent protein concentration, meaning that every 60 μL of enzyme solution contained 5 μg of protein (with a concentration of about 0.08 mg/mL). 60 μL of the enzyme solution was taken, diluted, then placed in a tube, and added with 440 μL of 30% (w/v) lactose substrate. The substrate and the enzyme solution were mixed as quickly as possible. All reactants were placed in a 200 rpm constant-temperature shaker to react for 6 h at a temperature of 50° C. After the reaction ended, the reaction product was boiled for 10 min in a 100° C. water bath to end the reaction, and then centrifuged for 10 min at 12,000 r/min.

The reaction product was diluted by 16 folds with ultra-purified water and then centrifuged for 10 min at 12,000 r/min, and 700 μL of the centrifuged product was taken to do the HPLC test.

Test Conditions of the High Performance Liquid Chromatograph (HPLC):

Before carrying out the quantitative test with the HPLC, standard curves of the glucose, galactose and lactose were drawn. The test ranges of the glucose, galactose and lactose were all 0-25.6 mg/mL. Test conditions included: Waters e2695 Separations Module; mobile phase: pure water with 50 mM EDTA calcium sodium salt; column temperature: 85° C.; flow rate: 0.5 mL/min, time: 12 min/sample.

Yield of oligosaccharide (mg/mL)=Initial amount of lactose (mg/mL)−Residual amount of lactose (mg/mL)−Amount of glucose (mg/mL)−Amount of galactose (mg/mL) (Jorgensen F et al, 2001).

GOS Conversion rate=Amount of oligosaccharide (mg/mL)/Initial amount of lactose (mg/mL).

Rate of GOS obtained by consuming lactose=Amount of oligosaccharide (mg/mL)/ [Initial amount of lactose (mg/mL)−Residual amount of lactose(mg/mL)].

Figure 4:
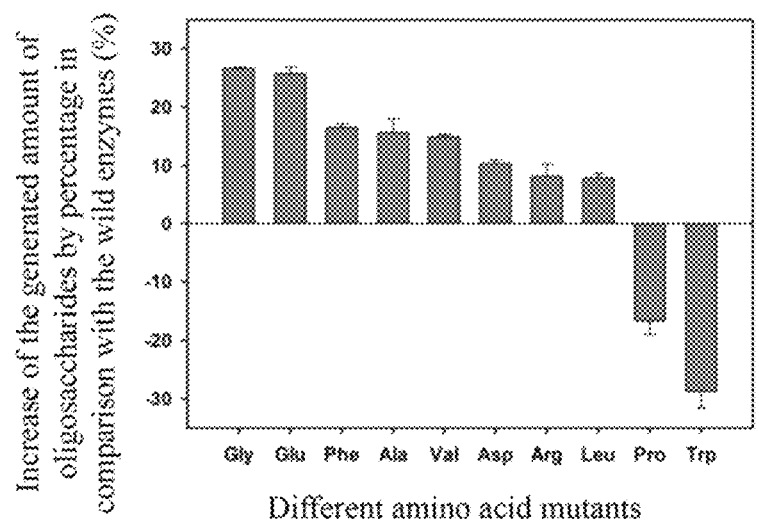
FIG. 4: Yield of GOS generated by typical mutants at site S219.

Embodiment 3: Screening of Saturation Mutation Library S219 and Synthesis of Oligosaccharides 200 positive *Pichia pastoris* clones were selected from the mutant library S219 to measure the transglycosidase activity and measure the nucleotide sequence. The sequence measurement result shows that, the mutants were respectively eight different types of amino acids all of which could enhance the transglycosidase activity of the mutant enzyme (see Table 3), in particular amino acids with smaller side chains, such as Gly, Ala, Val, and polarity amino acid Glu with negative charges, wherein the mutant Gly was most prominent (see FIG. 4), with an oligosaccharide yield increased by 26.6%. After the 5219 was mutated into Glu with small side chains and negative charges, the oligosaccharide yield was increased by 25.7%. After the 5219 was mutated into Ala and Val, the oligosaccharide yields were increased by 15.0% and 15.5%; after the 5219 was mutated into Asp, Arg and Leu, the oligosaccharide yields were respectively increased by 10.4%, 7.9% and 8.2%. After the 5219 was mutated into aromatic amino acid Phe with large side chains, the transglycosylation was also greatly enhanced by 16.4%. However, if the 5219 was mutated into Pro and Trp, the transglycosylation was obviously reduced by 16.7% and 28.7%, respectively. Thus it can be seen that, after the 5219 was mutated into other amino acids, the transglycosylation varied a lot, representing this site is an important site related to the transglycosylation of the β-galactosidase. In terms of protein structure, the site was positioned in the activity center-TIM barrel of the β-galactosidase. By the effect of charges and polarity, the site together with the lactose substrate generates a certain role, and the site is a non-conservation amino acid in the activity center.

TABLE 3

Oligosaccharides generated by different amino acid mutants of S219

| Different amino acid mutants | Mean amount of oligosaccharides generated (mg/mL) | Increase by percentage (%) in comparison with the wild enzymes |
| --- | --- | --- |
| WT (Ser) | 43.61 | 0 |
| Gly | 54.95 | 26.6 |
| Glu | 54.54 | 25.7 |
| Phe | 50.57 | 16.4 |
| Val | 49.93 | 15.5 |
| Ala | 50.17 | 15.0 |
| Asp | 47.96 | 10.4 |
| Leu | 46.92 | 8.2 |
| Arg | 47.02 | 7.9 |
| Pro | 36.34 | −16.7 |
| Trp | 31.17 | −28.7 |

Note:
WT represents wild enzyme.

Figure 5:
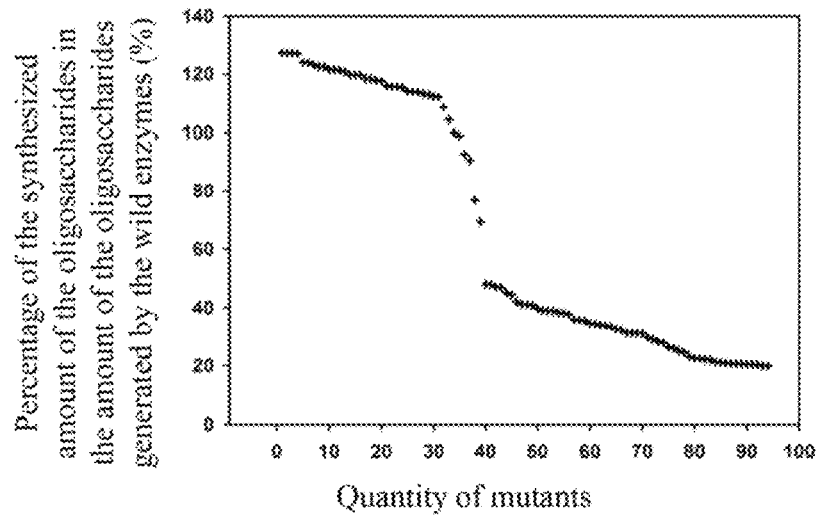
FIG. 5: Yield trend of the GOS in a mutant library at site F245.

Embodiment 4: Screening of the Saturation Mutation Library F245 and Synthesis of Oligosaccharides 200 positive mutants were selected from the library F245 to measure the transglycosidase activity. From the transglycosidase activity measurement result and the sequence measurement result show that, the mutants varied a lot in the aspect of oligosaccharide yield (see FIG. 5). The oligosaccharide yields of some mutants were greatly lower than those of the wild enzymes, and some were about 30% higher. Thus it can be seen that, F245 is also an important site related to the generation of the oligosaccharide by the β-galactosidase.

Figure 6:
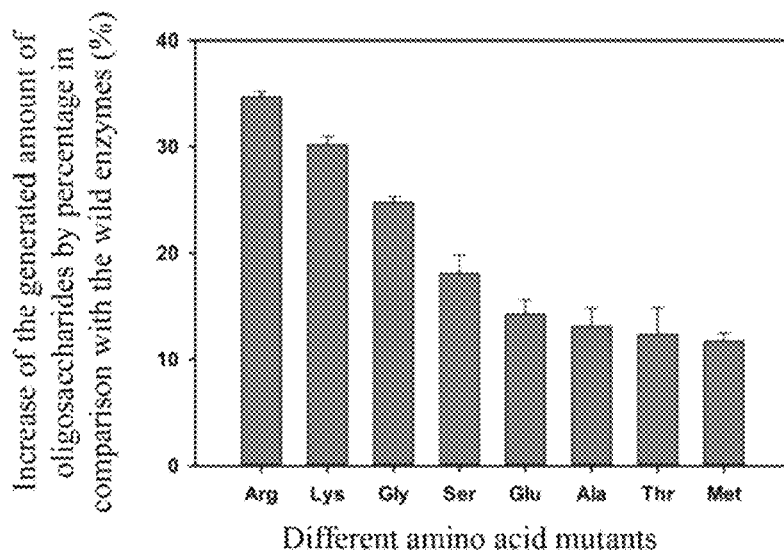
FIG. 6: Yield of GOS generated by typical mutants at site F245.

Specifically, after the site S245 was mutated into Arg, the oligosaccharide yield was maximum increased by about 35%, followed by Lys and Gly, increased by 30% and 24.7%, respectively. After the site F245 was mutated into other amino acids such as Ser, Glu, Ala, Thr and Met, the yield of the oligosaccharides was also increased (see FIG. 6).

Figure 7:
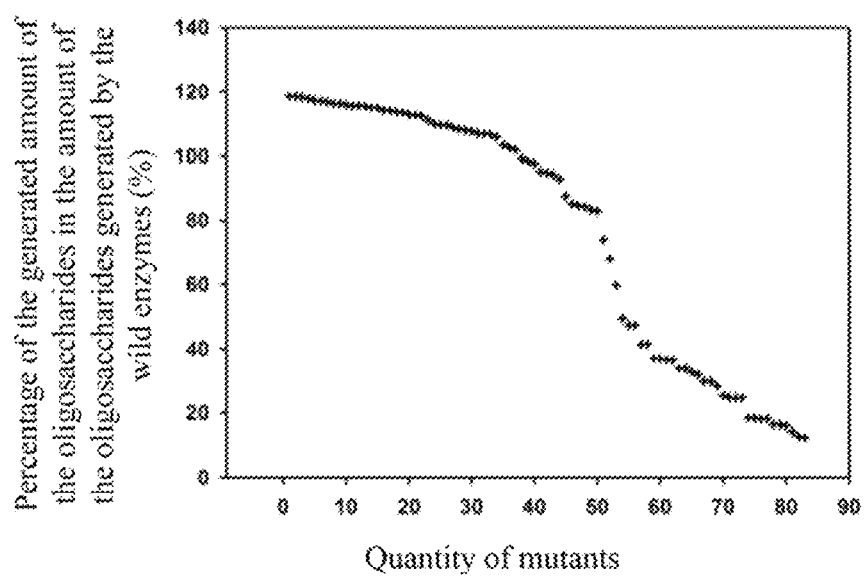
FIG. 7: Yield trend of the GOS in a mutant library at site E785.

Embodiment 5: Screening of the Saturation Mutation Library E785 and Synthesis of Oligosaccharides Compared with the wild types, in the E785 saturation mutant library, only a few mutants were increased in the yield of the oligosaccharides, and the increase was not greater than 20% (see FIG. 7). Among the mutants with increase in the oligosaccharide yield in the mutant library E785. After Glu was mutated to Val, the increase in the oligosaccharide yield was 15%, and the majority of the rest mutants had an oligosaccharide yield similar to that of the wild enzymes.

What is claimed is:

1. An artificial mutated β-galactosidase mutant, comprising an amino acid sequence set forth in SEQ ID NO: 2 or SEQ ID NO: 4 with at least one site mutation; wherein the site mutation is one or more selected from the group consisting of a first site mutation at position 219, a second site mutation at position 245 and a third site mutation at position 785;

wherein any random mutation at other positions excluding positions 219, 245 and 785 of the amino acid sequence is excluded;

wherein the site mutation is obtained by single-site-saturation mutation of β-galactosidase from *Aspergillus candidus* and *Aspergillus oryzae*, wherein a transglycosidase activity of the artificial mutated β-galactosidase mutant is at least 15% higher than that of a wild type.

2. An artificial mutated DNA molecule, wherein the artificial mutated DNA encodes the artificial mutated β-galactosidase mutant of claim 1.

3. A recombinant expression vector, comprising the DNA molecule of claim 2.

4. The recombinant expression vector of claim 3, wherein the recombinant expression vector is a recombinant yeast expression vector.

5. An isolated host cell comprising the recombinant expression vector of claim 4, wherein the host cell is selected from a group consisting of *saccharomyces, kluyveromyces, schizosaccharomyces* and methylotrophic yeasts.

6. A method for preparing an artificial mutated β-galactosidase mutant comprising the following steps:
   1) transforming a host cell using a recombinant expression vector comprising a DNA sequence encoding the artificial mutated β-galactosidase mutant to obtain a plurality of recombinant strains;
   2) culturing the plurality of recombinant strains, inducing the plurality of recombinant strains to express artificial mutated β-galactosidase mutant;
   3) gathering and purifying the artificial mutated β-galactosidase mutant;
   wherein the artificial mutated β-galactosidase mutant comprises an amino acid sequence set forth in SEQ ID NO: 2 or SEQ ID NO: 4 with at least one site mutation; wherein the site mutation is one or more selected from the group consisting of the first site mutation at position 219, the second site mutation at position 245 and the third site mutation at position 785:
   wherein any random mutation at other positions excluding positions 219, 245 and 785 of the amino acid sequence is excluded.

7. A method of preparing an artificial mutated β-galactosidase, comprising a step of transforming an isolated host cell with the recombinant expression vector of claim 3.

8. The artificial mutated β-galactosidase mutant of claim 1, wherein the first site mutation comprises a substitution of the serine by an amino acid selected from the group consisting of glycine, glutamic acid, phenylalanine, valine and alanine.

9. The artificial mutated β-galactosidase mutant of claim 1, wherein the second site mutation comprises a substitution of the phenylalanine by an amino acid selected from the group consisting of arginine, lysine, glycine and serine.

10. The artificial mutated β-galactosidase mutant of claim 1, wherein the third site mutation comprises a substitution of the glutamic acid by valine.

11. The artificial mutated β-galactosidase mutant of claim 1, wherein the transglycosidase activity of the artificial mutated β-galactosidase mutant is at least 20% higher than that of the wild type.

12. The artificial mutated β-galactosidase mutant of claim 1, wherein the transglycosidase activity of the artificial mutated β-galactosidase mutant is at least 30% higher than that of the wild type.

* * * * *

SEQUENCE LISTING

```
<160> NUMBER OF SEQ ID NOS: 17

<210> SEQ ID NO 1
<211> LENGTH: 2958
<212> TYPE: DNA
<213> ORGANISM: Artificial Sequence
<220> FEATURE:
<223> OTHER INFORMATION: The gene was cloned from Aspergillus candidus
      and its signal peptide sequence was removed
<220> FEATURE:
<221> NAME/KEY: gene
<222> LOCATION: (1)..(2958)

<400> SEQUENCE: 1
tccatcaagc atcgtctcaa tggcttcacg atcctggaac atccggatcc ggcgaaaaga        60
gacttgctgc aagacattgt tacatgggat gacaaatctc tgttcatcaa tggagagagg       120
attatgttat tcagcggaga agtgcatcct ttcagattgc cagtaccttc gctttggctt       180
gatatcttcc acaagatcag agctcttggt ttcaactgtg tatctttcta tattgattgg       240
gctcttctgg agggaaagcc tggcgactac agagcagaag gcatctttgc tctggaaccc       300
ttcttcgatg cagccaagga agcaggcatt tatctgatcg cccgccccgg ttcgtacatc       360
aatgccgagg tctcaggcgg tggcttccct ggatggttgc agagggtcaa tggcactctt       420
cgctcgtctg atgagccatt ccttaaagct actgataact atatcgccaa tgccgctgct       480
gccgtggcga aggctcaaat cacgaatgga gggccagtaa ttctctacca gcccgaaaac       540
gaatacagcg gtggctgctg cggtgtcaaa taccccgatg cagactacat gcagtatgtt       600
atggatcagg cccggaaggc tgacattgtt gtacctttca tcagcaacga tgcctcacct       660
tctgggcaca atgctcctgg aagtggaacg ggcgctgttg atatttatgg tcacgatagc       720
tatccccttg gctttgattg cgcaaaccca tccgtatggc ccgagggtaa actgcccgac       780
aacttccgca cgctccatct tgagcagagc ccatcaactc cgtattcact tcttgagttc       840
caagcgggtg ctttcgaccc atggggtgga cccggctttg aaaaatgcta tgccctcgtt       900
aaccacgaat tctcgagagt tttctatagg aacgacttga gtttcggagt ttctaccttt       960
aacttataca tgactttcgg cggaacaaac tggggtaacc tcggacatcc cggtggatat      1020
acatcctacg actacggctc gcctataact gaaacgcgaa acgttacacg ggagaagtac      1080
agcgacataa agctccttgc caactttgtc aaagcatcgc catcctatct caccgctact      1140
cccagaaacc tgactactgg tgtttacaca gacacatctg acctggctgt caccccgtta      1200
```

```
atgggtgata gtccaggctc attcttcgtg gtcagacata cggactattc cagccaagag    1260
tcaacctcgt acaaacttaa gcttcctacc agtgctggta acctgactat tccccagctg    1320
gagggcactc taagtctcaa cggacgtgac tcaaaaattc atgttgttga ttataatgtg    1380
tctggaacga acattatcta ttcgacagct gaagtcttca cctggaagaa gtttgacggt    1440
aacaaggtcc tggtgttata cggcggaccg aaggaacacc atgaattggc cattgcctcc    1500
aagtcaaatg tgaccatcat cgaaggttcg gactctggaa ttgtctcaac gaggaagggc    1560
agctctgtta tcattggctg ggatgtctct tctactcgtc gcatcgttca gtcggtgac     1620 ttgagagtgt tcctgcttga tagaaactct gcttacaact actgggtccc cgaactcccc    1680
acagaaggta cttctcccgg gttcagcact tcgaagacga ccgcctcctc cattattgtg    1740
aaggccggct acctcctccg aggggctcac ctggatggtg ctgatcttca tcttactgct    1800
gatttcaatg ccaccacccc gattgaagtg atcggtgctc aacaggcgc caagaatctg    1860 ttcgtgaatg gtgaaaaggc tagccacaca gtcgacaaaa acggcatctg gagtagtgag    1920
gtcaagtacg cggctccaga gatcaagctc cccggtttga aggatttgga ctggaagtat    1980
ctggacacgc ttcccgaaat taagtcttcc tatgatgact cggcctgggt ttcggcagac    2040
cttccaaaga caaagaacac tcaccgtcct cttgacacac aacatcgct atactcctct     2100 gactatggct ccacactgg ctacctgatc tacaggggtc acttcgttgc caacggcaag    2160
gaaagcgaat tttttattcg cacacaaggc ggtagcgcat cggaagttc cgtatggctg    2220 aacgagacgt atctgggctc ttggactggt gccgattatg cgatggacgg taactctacc    2280
tacaagctat ctcagctgga gtcgggcaag aattacgtca tcactgtggt tattgataac    2340
ctgggtctcg acgagaattg gacggtcggc gaggaaacca tgaagaatcc tcgtggtatt    2400
cttagctaca agctgagcgg acaagacgcc agcgcaatca cctggaagct cactggtaac    2460
ctcggaggag aagactacca ggataaggtt agaggacctc tcaacgaagg tggactgtac    2520
gcagagcgcc agggcttcca tcagcctcag cctccaagcg aatcctggga gtcgggcagt    2580
ccccttgaag gctgtcgaa gccgggtatc ggattctaca ctgcccagtt cgaccttgac    2640
ctcccgaagg gctgggatgt gccgctgtac ttcaactttg caacaacac ccaggcggct     2700 cgggcccagc tctacgtcaa cggttaccag tatggcaagt tcactggaaa cgttgggcca    2760
cagaccagct tccctgttcc cgaagggatc ctgaactacc gcggaaccaa ctatgtggca    2820
ctgagtcttt gggcattgga gtcggacggt gctaagctgg gtagcttcga actgtcctac    2880
accaccccag tgctgaccgg atacgggat gttgagtcac ctgagcagcc caagtatgag    2940
cagcggaagg gagcatac                                                 2958
```

<210> SEQ ID NO 2
<211> LENGTH: 986
<212> TYPE: PRT
<213> ORGANISM: Artificial Sequence
<220> FEATURE:
<223> OTHER INFORMATION: The coding gene of the protein was cloned from
      Aspergillus candidus and its signal peptide sequence was removed
<220> FEATURE:
<221> NAME/KEY: ACT_SITE
<222> LOCATION: (1)..(986)

<400> SEQUENCE: 2

Ser Ile Lys His Arg Leu Asn Gly Phe Thr Ile Leu Glu His Pro Asp
1               5                   10                  15

Pro Ala Lys Arg Asp Leu Leu Gln Asp Ile Val Thr Trp Asp Asp Lys
            20                  25                  30

```
Ser Leu Phe Ile Asn Gly Glu Arg Ile Met Leu Phe Ser Gly Glu Val
        35                  40                  45

His Pro Phe Arg Leu Pro Val Pro Ser Leu Trp Leu Asp Ile Phe His
    50                  55                  60

Lys Ile Arg Ala Leu Gly Phe Asn Cys Val Ser Phe Tyr Ile Asp Trp
65                  70                  75                  80

Ala Leu Leu Glu Gly Lys Pro Gly Asp Tyr Arg Ala Glu Gly Ile Phe
                85                  90                  95

Ala Leu Glu Pro Phe Phe Asp Ala Ala Lys Glu Ala Gly Ile Tyr Leu
            100                 105                 110

Ile Ala Arg Pro Gly Ser Tyr Ile Asn Ala Glu Val Ser Gly Gly Gly
        115                 120                 125

Phe Pro Gly Trp Leu Gln Arg Val Asn Gly Thr Leu Arg Ser Ser Asp
    130                 135                 140

Glu Pro Phe Leu Lys Ala Thr Asp Asn Tyr Ile Ala Asn Ala Ala Ala
145                 150                 155                 160

Ala Val Ala Lys Ala Gln Ile Thr Asn Gly Gly Pro Val Ile Leu Tyr
                165                 170                 175

Gln Pro Glu Asn Glu Tyr Ser Gly Gly Cys Cys Gly Val Lys Tyr Pro
            180                 185                 190

Asp Ala Asp Tyr Met Gln Tyr Val Met Asp Gln Ala Arg Lys Ala Asp
        195                 200                 205

Ile Val Val Pro Phe Ile Ser Asn Asp Ala Ser Pro Ser Gly His Asn
    210                 215                 220

Ala Pro Gly Ser Gly Thr Gly Ala Val Asp Ile Tyr Gly His Asp Ser
225                 230                 235                 240

Tyr Pro Leu Gly Phe Asp Cys Ala Asn Pro Ser Val Trp Pro Glu Gly
                245                 250                 255

Lys Leu Pro Asp Asn Phe Arg Thr Leu His Leu Glu Gln Ser Pro Ser
            260                 265                 270

Thr Pro Tyr Ser Leu Leu Glu Phe Gln Ala Gly Ala Phe Asp Pro Trp
        275                 280                 285

Gly Gly Pro Gly Phe Glu Lys Cys Tyr Ala Leu Val Asn His Glu Phe
    290                 295                 300

Ser Arg Val Phe Tyr Arg Asn Asp Leu Ser Phe Gly Val Ser Thr Phe
305                 310                 315                 320

Asn Leu Tyr Met Thr Phe Gly Gly Thr Asn Trp Gly Asn Leu Gly His
                325                 330                 335

Pro Gly Gly Tyr Thr Ser Tyr Asp Tyr Gly Ser Pro Ile Thr Glu Thr
            340                 345                 350

Arg Asn Val Thr Arg Glu Lys Tyr Ser Asp Ile Lys Leu Leu Ala Asn
        355                 360                 365

Phe Val Lys Ala Ser Pro Ser Tyr Leu Thr Ala Thr Pro Arg Asn Leu
    370                 375                 380

Thr Thr Gly Val Tyr Thr Asp Thr Ser Asp Leu Ala Val Thr Pro Leu
385                 390                 395                 400

Met Gly Asp Ser Pro Gly Ser Phe Phe Val Val Arg His Thr Asp Tyr
                405                 410                 415

Ser Ser Gln Glu Ser Thr Ser Tyr Lys Leu Lys Leu Pro Thr Ser Ala
            420                 425                 430

Gly Asn Leu Thr Ile Pro Gln Leu Glu Gly Thr Leu Ser Leu Asn Gly
        435                 440                 445
```

-continued

```
Arg Asp Ser Lys Ile His Val Val Asp Tyr Asn Val Ser Gly Thr Asn
450                 455                 460
Ile Ile Tyr Ser Thr Ala Glu Val Phe Thr Trp Lys Lys Phe Asp Gly
465                 470                 475                 480
Asn Lys Val Leu Val Leu Tyr Gly Gly Pro Lys Glu His His Glu Leu
                485                 490                 495
Ala Ile Ala Ser Lys Ser Asn Val Thr Ile Ile Glu Gly Ser Asp Ser
                500                 505                 510
Gly Ile Val Ser Thr Arg Lys Gly Ser Ser Val Ile Ile Gly Trp Asp
                515                 520                 525
Val Ser Ser Thr Arg Arg Ile Val Gln Val Gly Asp Leu Arg Val Phe
530                 535                 540
Leu Leu Asp Arg Asn Ser Ala Tyr Asn Tyr Trp Val Pro Glu Leu Pro
545                 550                 555                 560
Thr Glu Gly Thr Ser Pro Gly Phe Ser Thr Ser Lys Thr Thr Ala Ser
                565                 570                 575
Ser Ile Ile Val Lys Ala Gly Tyr Leu Leu Arg Gly Ala His Leu Asp
                580                 585                 590
Gly Ala Asp Leu His Leu Thr Ala Asp Phe Asn Ala Thr Thr Pro Ile
                595                 600                 605
Glu Val Ile Gly Ala Pro Thr Gly Ala Lys Asn Leu Phe Val Asn Gly
610                 615                 620
Glu Lys Ala Ser His Thr Val Asp Lys Asn Gly Ile Trp Ser Ser Glu
625                 630                 635                 640
Val Lys Tyr Ala Ala Pro Glu Ile Lys Leu Pro Gly Leu Lys Asp Leu
                645                 650                 655
Asp Trp Lys Tyr Leu Asp Thr Leu Pro Glu Ile Lys Ser Ser Tyr Asp
                660                 665                 670
Asp Ser Ala Trp Val Ser Ala Asp Leu Pro Lys Thr Lys Asn Thr His
                675                 680                 685
Arg Pro Leu Asp Thr Pro Thr Ser Leu Tyr Ser Asp Tyr Gly Phe
690                 695                 700
His Thr Gly Tyr Leu Ile Tyr Arg Gly His Phe Val Ala Asn Gly Lys
705                 710                 715                 720
Glu Ser Glu Phe Phe Ile Arg Thr Gln Gly Gly Ser Ala Phe Gly Ser
                725                 730                 735
Ser Val Trp Leu Asn Glu Thr Tyr Leu Gly Ser Trp Thr Gly Ala Asp
                740                 745                 750
Tyr Ala Met Asp Gly Asn Ser Thr Tyr Lys Leu Ser Gln Leu Glu Ser
                755                 760                 765
Gly Lys Asn Tyr Val Ile Thr Val Val Ile Asp Asn Leu Gly Leu Asp
770                 775                 780
Glu Asn Trp Thr Val Gly Glu Thr Met Lys Asn Pro Arg Gly Ile
785                 790                 795                 800
Leu Ser Tyr Lys Leu Ser Gly Gln Asp Ala Ser Ala Ile Thr Trp Lys
                805                 810                 815
Leu Thr Gly Asn Leu Gly Gly Glu Asp Tyr Gln Asp Lys Val Arg Gly
                820                 825                 830
Pro Leu Asn Glu Gly Gly Leu Tyr Ala Glu Arg Gln Gly Phe His Gln
                835                 840                 845
Pro Gln Pro Pro Ser Glu Ser Trp Glu Ser Gly Ser Pro Leu Glu Gly
850                 855                 860
Leu Ser Lys Pro Gly Ile Gly Phe Tyr Thr Ala Gln Phe Asp Leu Asp
```

```
                   865                 870                 875                 880

Leu Pro Lys Gly Trp Asp Val Pro Leu Tyr Phe Asn Phe Gly Asn Asn
                        885                 890                 895

Thr Gln Ala Ala Arg Ala Gln Leu Tyr Val Asn Gly Tyr Gln Tyr Gly
                900                 905                 910

Lys Phe Thr Gly Asn Val Gly Pro Gln Thr Ser Phe Pro Val Pro Glu
                915                 920                 925

Gly Ile Leu Asn Tyr Arg Gly Thr Asn Tyr Val Ala Leu Ser Leu Trp
        930                 935                 940

Ala Leu Glu Ser Asp Gly Ala Lys Leu Gly Ser Phe Glu Leu Ser Tyr
945                 950                 955                 960

Thr Thr Pro Val Leu Thr Gly Tyr Gly Asp Val Glu Ser Pro Glu Gln
                965                 970                 975

Pro Lys Tyr Glu Gln Arg Lys Gly Ala Tyr
                980                 985
```

<210> SEQ ID NO 3
<211> LENGTH: 2958
<212> TYPE: DNA
<213> ORGANISM: Artificial Sequence
<220> FEATURE:
<223> OTHER INFORMATION: The gene was cloned from Aspergillus oryze and
      its signal peptide sequence was removed
<220> FEATURE:
<221> NAME/KEY: gene
<222> LOCATION: (1)..(2958)

<400> SEQUENCE: 3

| | | |
|---|---|---|
| tccatcaagc atcgtctcaa tggcttcacg atcctggaac atccggatcc ggcgaaaaga | 60 |
| gacttgctgc aagacattgt tacatgggat gacaaatctc tgttcatcaa tggagagagg | 120 |
| attatgttat tcagcggaga agtgcatcct ttcagattgc cagtaccttc gctttggctt | 180 |
| gatatcttcc acaagatcag agctcttggt ttcaactgtg tatctttcta tattgattgg | 240 |
| gctcttctgg agggaaagcc tggcgactac agagcagaag gcatctttgc tctggaaccc | 300 |
| ttctttgatg cagccaagga agcaggcatt tatctgatcg cccgccccgg ttcgtacatc | 360 |
| aatgccgagg tctcaggcgg tggcttccct ggatggttgc agagggtcaa tggcactctt | 420 |
| cgctcgtctg atgagccatt ccttaaagct actgataact atatcgccaa tgccgctgct | 480 |
| gccgtggcga aggctcaaat cacgaatgga gggccagtaa ttctctacca gcccgaaaac | 540 |
| gaatacagcg gtggctgctg cggtgtcaaa taccccgatg cagactacat gcagtatgtt | 600 |
| atggatcagg cccggaaggc tgacattgtt gtaccttca tcagcaacga tgcctcacct | 660 |
| tctgggcaca tgctcctgg aagtggaacg agcgctgttg atatttatgg tcacgatagc | 720 |
| tatcccctcg gctttgattg cgcaaaccca tccgtatggc ccgagggtaa actgcccgac | 780 |
| aacttccgca cgctccatct tgagcagagc ccatcaactc cgtattcact tcttgagttc | 840 |
| caagcgggtg ctttcgaccc atgggtgga cccggctttg aaaatgcta tgccctcgtt | 900 |
| aaccacgaat tctcgagagt tttctatagg aacgacttga gtttcggagt ttctaccttt | 960 |
| aacttataca tgactttcgg cggaacaaac tggggtaacc tcggacatcc cggtggatat | 1020 |
| acatcctacg actacggatc gcctataact gaaacgcgaa acgttacgcg ggagaagtac | 1080 |
| agcgacataa agctccttgc caactttgtc aaagcatcgc catcctatct caccgctact | 1140 |
| cccagaaacc tgactactgg tgtttacaca gacacatctg acctggctgt caccccgtta | 1200 |
| attggtgata gtccaggctc attcttcgtg gtcagacata cggactattc cagccaagag | 1260 |

```
tcaacctcgt acaaacttaa gcttcctacc agtgctggta acctgactat tccccagctg    1320
gagggcactc taagtctcaa cggacgtgac tcaaaaattc atgttgttga ttataatgtg    1380
tctggaacga acattatcta ttcgacagct gaagtcttca cctggaagaa gtttgacggt    1440
aacaaggtcc tggtgttata cggcggaccg aaggaacacc atgaattggc cattgcctcc    1500
aagtcaaatg tgaccatcat cgaaggttcg gactctggaa ttgtctcaac gaggaagggc    1560
agctctgtta tcattggctg ggatgtctct tctactcgtc gcatcgttca agtcggtgac    1620
ttgagagtgt tcctgcttga taggaactct gcttacaact actgggtccc cgaactcccc    1680
acagaaggta cttctcccgg gttcagcact tcgaagacga ccgcctcctc cattattgtg    1740
aaggctggct acctcctccg aggcgctcac cttgatggtg ctgatcttca tcttactgct    1800
gatttcaatg ccaccacccc gattgaagtg atcggtgctc aacaggcgc taagaatctg    1860
ttcgtgaatg gtgaaaaggc tagccacaca gtcgacaaga acggcatctg gagcagtgag    1920
gtcaagtacg cggctccaga gatcaagctc cccggtttga aggatttgga ctggaagtat    1980
ctggacacgc ttcccgaaat taagtcttcc tatgatgact cggcctgggt ttcggcagac    2040
cttccaaaga caaagaacac tcaccgtcct cttgacacac caacatcgct atactcctct    2100
gactatggct tccacactgg ctacctgatc tacaggggtc acttcgttgc caacggcaag    2160
gaaagcgaat tttttattcg cacacaaggc ggtagcgcat tcggaagttc cgtatggctg    2220
aacgagacgt atctgggctc ttggactggt gccgattatg cgatggacgg taactctacc    2280
tacaagctat ctcagctgga gtcgggcaag aattacgtca tcactgtggt tattgataac    2340
ctgggtctcg acgagaattg gacggtcggc gaggaaacca tgaagaatcc tcgtggtatt    2400
cttagctaca agctgagcgg acaagacgcc agcgcaatca cctggaagct cactggtaac    2460
ctcggaggag aagactacca ggataaggtt agaggacctc tcaacgaagg tggactgtac    2520
gcagagcgcc agggcttcca tcagcctcag cctccaagcg aatcctggga gtcgggcagt    2580
ccccttgaag gcctgtcgaa gccgggtatc ggattctaca ctgcccagtt cgaccttgac    2640
ctcccgaagg gctgggatgt gccgctgtac ttcaactttg caacaacac ccaggcggct    2700
cgggcccagc tctacgtcaa cggttaccag tatggcaagt tcactggaaa cgttgggcca    2760
cagaccagct tccctgttcc cgaaggtatc ctgaactacc gcggaaccaa ctatgtggca    2820
ctgagtcttt gggcattgga gtcggacggt gctaagctgg gtagcttcga actgtcctac    2880
accaccccag tgctgaccgg atacgggaat gttgagtcac ctgagcagcc caagtatgag    2940
cagcggaagg gagcatac                                                 2958
```

<210> SEQ ID NO 4
<211> LENGTH: 986
<212> TYPE: PRT
<213> ORGANISM: Artificial Sequence
<220> FEATURE:
<223> OTHER INFORMATION: The coding gene of the protein was cloned from
      Aspergillus oryze and its signal peptide sequence was removed
<220> FEATURE:
<221> NAME/KEY: ACT_SITE
<222> LOCATION: (1)..(986)

<400> SEQUENCE: 4

Ser Ile Lys His Arg Leu Asn Gly Phe Thr Ile Leu Glu His Pro Asp
1               5                   10                  15

Pro Ala Lys Arg Asp Leu Leu Gln Asp Ile Val Thr Trp Asp Asp Lys
            20                  25                  30

Ser Leu Phe Ile Asn Gly Glu Arg Ile Met Leu Phe Ser Gly Glu Val

```
                35                  40                  45
His Pro Phe Arg Leu Pro Val Pro Ser Leu Trp Leu Asp Ile Phe His
 50                  55                  60

Lys Ile Arg Ala Leu Gly Phe Asn Cys Val Ser Phe Tyr Ile Asp Trp
 65                  70                  75                  80

Ala Leu Leu Glu Gly Lys Pro Gly Asp Tyr Arg Ala Glu Gly Ile Phe
                 85                  90                  95

Ala Leu Glu Pro Phe Phe Asp Ala Ala Lys Glu Ala Gly Ile Tyr Leu
            100                 105                 110

Ile Ala Arg Pro Gly Ser Tyr Ile Asn Ala Glu Val Ser Gly Gly Gly
        115                 120                 125

Phe Pro Gly Trp Leu Gln Arg Val Asn Gly Thr Leu Arg Ser Ser Asp
    130                 135                 140

Glu Pro Phe Leu Lys Ala Thr Asp Asn Tyr Ile Ala Asn Ala Ala Ala
145                 150                 155                 160

Ala Val Ala Lys Ala Gln Ile Thr Asn Gly Gly Pro Val Ile Leu Tyr
                165                 170                 175

Gln Pro Glu Asn Glu Tyr Ser Gly Gly Cys Cys Gly Val Lys Tyr Pro
            180                 185                 190

Asp Ala Asp Tyr Met Gln Tyr Val Met Asp Gln Ala Arg Lys Ala Asp
        195                 200                 205

Ile Val Val Pro Phe Ile Ser Asn Asp Ala Ser Pro Ser Gly His Asn
    210                 215                 220

Ala Pro Gly Ser Gly Thr Ser Ala Val Asp Ile Tyr Gly His Asp Ser
225                 230                 235                 240

Tyr Pro Leu Gly Phe Asp Cys Ala Asn Pro Ser Val Trp Pro Glu Gly
                245                 250                 255

Lys Leu Pro Asp Asn Phe Arg Thr Leu His Leu Glu Gln Ser Pro Ser
            260                 265                 270

Thr Pro Tyr Ser Leu Leu Glu Phe Gln Ala Gly Ala Phe Asp Pro Trp
        275                 280                 285

Gly Gly Pro Gly Phe Glu Lys Cys Tyr Ala Leu Val Asn His Glu Phe
    290                 295                 300

Ser Arg Val Phe Tyr Arg Asn Asp Leu Ser Phe Gly Val Ser Thr Phe
305                 310                 315                 320

Asn Leu Tyr Met Thr Phe Gly Gly Thr Asn Trp Gly Asn Leu Gly His
                325                 330                 335

Pro Gly Gly Tyr Thr Ser Tyr Asp Tyr Gly Ser Pro Ile Thr Glu Thr
            340                 345                 350

Arg Asn Val Thr Arg Glu Lys Tyr Ser Asp Ile Lys Leu Leu Ala Asn
        355                 360                 365

Phe Val Lys Ala Ser Pro Ser Tyr Leu Thr Ala Thr Pro Arg Asn Leu
    370                 375                 380

Thr Thr Gly Val Tyr Thr Asp Thr Ser Asp Leu Ala Val Thr Pro Leu
385                 390                 395                 400

Ile Gly Asp Ser Pro Gly Ser Phe Phe Val Val Arg His Thr Asp Tyr
                405                 410                 415

Ser Ser Gln Glu Ser Thr Ser Tyr Lys Leu Lys Leu Pro Thr Ser Ala
            420                 425                 430

Gly Asn Leu Thr Ile Pro Gln Leu Glu Gly Thr Leu Ser Leu Asn Gly
        435                 440                 445

Arg Asp Ser Lys Ile His Val Val Asp Tyr Asn Val Ser Gly Thr Asn
    450                 455                 460
```

```
Ile Ile Tyr Ser Thr Ala Glu Val Phe Thr Trp Lys Lys Phe Asp Gly
465                 470                 475                 480

Asn Lys Val Leu Val Leu Tyr Gly Gly Pro Lys Glu His His Glu Leu
                485                 490                 495

Ala Ile Ala Ser Lys Ser Asn Val Thr Ile Ile Glu Gly Ser Asp Ser
                500                 505                 510

Gly Ile Val Ser Thr Arg Lys Gly Ser Ser Val Ile Ile Gly Trp Asp
                515                 520                 525

Val Ser Ser Thr Arg Arg Ile Val Gln Val Gly Asp Leu Arg Val Phe
530                 535                 540

Leu Leu Asp Arg Asn Ser Ala Tyr Asn Tyr Trp Val Pro Glu Leu Pro
545                 550                 555                 560

Thr Glu Gly Thr Ser Pro Gly Phe Ser Thr Ser Lys Thr Thr Ala Ser
                565                 570                 575

Ser Ile Ile Val Lys Ala Gly Tyr Leu Leu Arg Gly Ala His Leu Asp
                580                 585                 590

Gly Ala Asp Leu His Leu Thr Ala Asp Phe Asn Ala Thr Pro Ile
                595                 600                 605

Glu Val Ile Gly Ala Pro Thr Gly Ala Lys Asn Leu Phe Val Asn Gly
                610                 615                 620

Glu Lys Ala Ser His Thr Val Asp Lys Asn Gly Ile Trp Ser Ser Glu
625                 630                 635                 640

Val Lys Tyr Ala Ala Pro Glu Ile Lys Leu Pro Gly Leu Lys Asp Leu
                645                 650                 655

Asp Trp Lys Tyr Leu Asp Thr Leu Pro Glu Ile Lys Ser Ser Tyr Asp
                660                 665                 670

Asp Ser Ala Trp Val Ser Ala Asp Leu Pro Lys Thr Lys Asn Thr His
                675                 680                 685

Arg Pro Leu Asp Thr Pro Thr Ser Leu Tyr Ser Ser Asp Tyr Gly Phe
690                 695                 700

His Thr Gly Tyr Leu Ile Tyr Arg Gly His Phe Val Ala Asn Gly Lys
705                 710                 715                 720

Glu Ser Glu Phe Phe Ile Arg Thr Gln Gly Gly Ser Ala Phe Gly Ser
                725                 730                 735

Ser Val Trp Leu Asn Glu Thr Tyr Leu Gly Ser Trp Thr Gly Ala Asp
                740                 745                 750

Tyr Ala Met Asp Gly Asn Ser Thr Tyr Lys Leu Ser Gln Leu Glu Ser
                755                 760                 765

Gly Lys Asn Tyr Val Ile Thr Val Val Ile Asp Asn Leu Gly Leu Asp
                770                 775                 780

Glu Asn Trp Thr Val Gly Glu Glu Thr Met Lys Asn Pro Arg Gly Ile
785                 790                 795                 800

Leu Ser Tyr Lys Leu Ser Gly Gln Asp Ala Ser Ala Ile Thr Trp Lys
                805                 810                 815

Leu Thr Gly Asn Leu Gly Gly Glu Asp Tyr Gln Asp Lys Val Arg Gly
                820                 825                 830

Pro Leu Asn Glu Gly Gly Leu Tyr Ala Glu Arg Gln Gly Phe His Gln
                835                 840                 845

Pro Gln Pro Pro Ser Glu Ser Trp Glu Ser Gly Ser Pro Leu Glu Gly
                850                 855                 860

Leu Ser Lys Pro Gly Ile Gly Phe Tyr Thr Ala Gln Phe Asp Leu Asp
865                 870                 875                 880
```

```
Leu Pro Lys Gly Trp Asp Val Pro Leu Tyr Phe Asn Phe Gly Asn Asn
                885                 890                 895

Thr Gln Ala Ala Arg Ala Gln Leu Tyr Val Asn Gly Tyr Gln Tyr Gly
            900                 905                 910

Lys Phe Thr Gly Asn Val Gly Pro Gln Thr Ser Phe Pro Val Pro Glu
        915                 920                 925

Gly Ile Leu Asn Tyr Arg Gly Thr Asn Tyr Val Ala Leu Ser Leu Trp
    930                 935                 940

Ala Leu Glu Ser Asp Gly Ala Lys Leu Gly Ser Phe Glu Leu Ser Tyr
945                 950                 955                 960

Thr Thr Pro Val Leu Thr Gly Tyr Gly Asn Val Glu Ser Pro Glu Gln
                965                 970                 975

Pro Lys Tyr Glu Gln Arg Lys Gly Ala Tyr
                980                 985

<210> SEQ ID NO 5
<211> LENGTH: 32
<212> TYPE: DNA
<213> ORGANISM: Artificial Sequence
<220> FEATURE:
<223> OTHER INFORMATION: primers of PCR
<220> FEATURE:
<221> NAME/KEY: gene
<222> LOCATION: (1)..(32)

<400> SEQUENCE: 5
cgcgaggcag agatcttgag ataaatttca cg                                 32

<210> SEQ ID NO 6
<211> LENGTH: 33
<212> TYPE: DNA
<213> ORGANISM: Artificial Sequence
<220> FEATURE:
<223> OTHER INFORMATION: primers of PCR
<220> FEATURE:
<221> NAME/KEY: gene
<222> LOCATION: (1)..(33)

<400> SEQUENCE: 6
acgtgaaatt tatctcaaga tctctgcctc gcg                                33

<210> SEQ ID NO 7
<211> LENGTH: 40
<212> TYPE: DNA
<213> ORGANISM: Artificial Sequence
<220> FEATURE:
<223> OTHER INFORMATION: primers of PCR
<220> FEATURE:
<221> NAME/KEY: misc_feature
<222> LOCATION: (29)..(30)
<223> OTHER INFORMATION: n is a, c, g, or t

<400> SEQUENCE: 7
acttccagga gcattgtgcc cagaaggmnn ggcatcgttg                         40

<210> SEQ ID NO 8
<211> LENGTH: 31
<212> TYPE: DNA
<213> ORGANISM: Artificial Sequence
<220> FEATURE:
<223> OTHER INFORMATION: primers of PCR
<220> FEATURE:
<221> NAME/KEY: gene
<222> LOCATION: (1)..(31)

<400> SEQUENCE: 8
```
ttctgggcac aatgctcctg gaagtggaac g    31

<210> SEQ ID NO 9
<211> LENGTH: 36
<212> TYPE: DNA
<213> ORGANISM: Artificial Sequence
<220> FEATURE:
<223> OTHER INFORMATION: primers of PCR
<220> FEATURE:
<221> NAME/KEY: misc_feature
<222> LOCATION: (29)..(30)
<223> OTHER INFORMATION: n is a, c, g, or t

<400> SEQUENCE: 9
tgcgcaatca aagccaaggg gatagctmnn gtgacc    36

<210> SEQ ID NO 10
<211> LENGTH: 27
<212> TYPE: DNA
<213> ORGANISM: Artificial Sequence
<220> FEATURE:
<223> OTHER INFORMATION: primers of PCR
<220> FEATURE:
<221> NAME/KEY: gene
<222> LOCATION: (1)..(27)

<400> SEQUENCE: 10
tccccttggc tttgattgcg caaaccc    27

<210> SEQ ID NO 11
<211> LENGTH: 36
<212> TYPE: DNA
<213> ORGANISM: Artificial Sequence
<220> FEATURE:
<223> OTHER INFORMATION: primers of PCR
<220> FEATURE:
<221> NAME/KEY: misc_feature
<222> LOCATION: (26)..(27)
<223> OTHER INFORMATION: n is a, c, g, or t

<400> SEQUENCE: 11
tgcgcaatca aagccaaggg gatamnnatc gtgacc    36

<210> SEQ ID NO 12
<211> LENGTH: 32
<212> TYPE: DNA
<213> ORGANISM: Artificial Sequence
<220> FEATURE:
<223> OTHER INFORMATION: primers of PCR
<220> FEATURE:
<221> NAME/KEY: misc_feature
<222> LOCATION: (25)..(26)
<223> OTHER INFORMATION: n is a, c, g, or t

<400> SEQUENCE: 12
tttgcgcaat caaagccaag gggmnngcta tc    32

<210> SEQ ID NO 13
<211> LENGTH: 30
<212> TYPE: DNA
<213> ORGANISM: Artificial Sequence
<220> FEATURE:
<223> OTHER INFORMATION: primers of PCR
<220> FEATURE:
<221> NAME/KEY: gene
<222> LOCATION: (1)..(30)

<400> SEQUENCE: 13

```
<210> SEQ ID NO 14
<211> LENGTH: 31
<212> TYPE: DNA
<213> ORGANISM: Artificial Sequence
<220> FEATURE:
<223> OTHER INFORMATION: primers of PCR
<220> FEATURE:
<221> NAME/KEY: misc_feature
<222> LOCATION: (24)..(25)
<223> OTHER INFORMATION: n is a, c, g, or t

<400> SEQUENCE: 14
atacggatgg gtttgcgcaa tcmnngccaa g                              31

<210> SEQ ID NO 15
<211> LENGTH: 24
<212> TYPE: DNA
<213> ORGANISM: Artificial Sequence
<220> FEATURE:
<223> OTHER INFORMATION: primers of PCR
<220> FEATURE:
<221> NAME/KEY: gene
<222> LOCATION: (1)..(24)

<400> SEQUENCE: 15
tgcgcaaacc catccgtatg gccc                                      24

<210> SEQ ID NO 16
<211> LENGTH: 29
<212> TYPE: DNA
<213> ORGANISM: Artificial Sequence
<220> FEATURE:
<223> OTHER INFORMATION: primers of PCR
<220> FEATURE:
<221> NAME/KEY: gene
<222> LOCATION: (1)..(29)

<400> SEQUENCE: 16
tttcctcgcc gaccgtccaa ttaacgtcg                                 29

<210> SEQ ID NO 17
<211> LENGTH: 27
<212> TYPE: DNA
<213> ORGANISM: Artificial Sequence
<220> FEATURE:
<223> OTHER INFORMATION: primers of PCR
<220> FEATURE:
<221> NAME/KEY: gene
<222> LOCATION: (1)..(27)

<400> SEQUENCE: 17
tggacggtcg gcgaggaaac catgaag                                   27
```